United States Patent [19]

Weil

[11] 4,086,303

[45] Apr. 25, 1978

[54] COPOLYCONDENSATION PRODUCTS OF β-HALOALKYL PHOSPHATES AND DIALKYL PHOSPHONATES

[75] Inventor: Edward D. Weil, Hastings-on-Hudson, N.Y.

[73] Assignee: Stauffer Chemical Company, Westport, Conn.

[21] Appl. No.: 811,972

[22] Filed: Jul. 5, 1977

Related U.S. Application Data

[63] Continuation-in-part of Ser. No. 783,995, Apr. 4, 1977, abandoned, which is a continuation-in-part of Ser. No. 558,862, Mar. 17, 1975, abandoned, which is a continuation-in-part of Ser. No. 410,583, Nov. 12, 1973, abandoned.

[51] Int. Cl.$^2$ ............................ C07F 9/40; C08J 9/00; C08K 5/53

[52] U.S. Cl. .............................. 260/928; 260/2.5 AJ; 260/45.7 P

[58] Field of Search .................................. 260/928, 929

[56] References Cited

U.S. PATENT DOCUMENTS 3,891,727   6/1975   Weil ..................................... 260/928

Primary Examiner—Anton H. Sutto
Attorney, Agent, or Firm—Richard P. Fennelly

[57] ABSTRACT

Copolycondensation products of β-haloalkyl phosphates and dialkyl phosphonates are useful fire retardant agents. The products are prepared by heating the starting materials at a temperature of about 110° to 250° C., preferably in the presence of a nucleophilic catalyst, until at least one mole of alkyl halide per mole of phosphonate is driven off. Preferred are copolycondensation products obtained by substantially complete removal of halogen as alkyl halide.

25 Claims, No Drawings

COPOLYCONDENSATION PRODUCTS OF β-HALOALKYL PHOSPHATES AND DIALKYL PHOSPHONATES

This application is a continuation-in part of U.S. Ser. No. 783,995, filed Apr. 4, 1977, which, in turn, is a continuation-in-part of U.S. Ser. No. 558,862, filed Mar. 17, 1975, which, in turn, is a continuation-in-part of U.S. Ser. No. 410,583, filed Nov. 12, 1973, all now abandoned.

This invention relates to condensation products of β-haloalkyl phosphates and dialkyl phosphonates and to their use as fire retardants for urethane foams, polyesters and other flammable polymers and textiles. More particularly, it relates to copolycondensation products of β-haloalkyl phosphates having from 2 to 4 carbon atoms in the alkyl moiety and dialkyl phosphonates, said products being obtained by heating the starting materials in the presence of a nucleophilic catalyst.

β-haloalkyl phosphates, particularly tris(2-haloethyl) phosphates such as tris(2-chloroethyl)phosphate, are known compounds and have been used as fire retardant agents in various flammable polymers such as polyurethane foams. The fire retardant properties of tris(2-haloethyl) phosphates have been significantly improved by the recent development of a condensation process to obtain liquid poly(haloethyl-ethyleneoxy) phosphates. These phosphates and the method for their preparation are more fully described in U.S. Pat. No. 3,896,187, which issued on July 22, 1975. The reaction involves a homopolycondensation, in the presence of a basic catalyst, with loss of ethylene dichloride and formation of oligomeric phosphates. This homopolycondensation reaction, however, has certain limitations. For example, it is virtually impossible by this reaction to prepare liquid products having more than above 15% phosphorus.

It is an object of this invention to prepare phosphorous-containing flame retardant agents having a phosphorus content greater than 15%. Additionally, the homopolycondensation reaction cannot be driven to completion, i.e., removal of all of the halogen, without gelation of the product. Thus, where excellent non-corrosive and/or extremely good electrical properties are desired, one cannot obtain the necessary non-halogen containing product. Furthermore, since all of the halogen cannot be removed, the product can continue to give off volatile halogenated fragments during fabrication or during use in a plastic. Such volatile fragments represent undesirable air pollutants. It is a further object of the present invention to obtain, in a preferred embodiment, a non-halogen containing and non-gelling condensation product.

By the prior art homopolycondensation of tris(2-haloethyl) phosphates, it has not been possible to prepare water soluble phosphorus-rich non-volatile flame retardant products suitable for aqueous textile finishing processes. It is therefore another object of this invention to make available such water-soluble phosphorus-rich non-volatile products.

It has now been found that copolycondensation of a β-haloalkyl phosphate and a dialkyl phosphonate yields a condensation product which can be of low halogen content or even free of halogen, is resistant to gelation, and is higher in phosphorus content than homopolycondensed β-haloalkyl phosphates. Furthermore, these products are highly effective fire retardant additives for urethane foams, polyesters and other flammable polymers and textiles. These copolycondensation products are obtained by heating the starting materials together until at least about one molar equivalent of alkyl halide is released, generally at a temperature within the range of about 110° to 250° C., preferably 120° to 230° C., and preferably in the presence of a nucleophilic catalyst. In most instances, the products obtained are clear liquids of little or no color and odor and are thus suitable for a variety of fire retardant uses.

The β-haloalkyl phosphates usable in the practice of this invention contain at least one haloalkyl group of from 2 to 4 carbon atoms, preferably a 2-haloethyl group. Preferred, because of their reactivity, are the tris-haloalkyl phosphates particularly the tris(2-haloethyl) phosphates in which the halogen is chlorine or bromine. Most preferred is tris(2-chloroethyl) phosphate, athough tris(β-chloroisopropyl)phosphate, tris(β,β'-dichloroisopropyl) phosphate and tris (2,3-dibromo-n-propyl) phosphate are also quite satisfactory for use. Also usable are the polycondensed 2-haloalkyl phosphates of abandoned application Ser. No. 164,928, filed July 21, 1971, now abandoned, tetrakis (2-haloalkyl) alkylene diphosphates, hexakis (2-haloalkyl) trimethylol alkane triphosphates and the like.

Where a mono(β-haloalkyl) phosphate or a bis(β-haloalkyl) phosphate ester is used, the remaining ester groups can be any organic radicals which do not interfere with the polycondensation reaction. For example, these can be alkyl groups of from 1 to 20 carbon atoms, particularly alkyl groups of from 1 to 4 carbon atoms; aryls, e.g., phenyl; alkyl substituted by non-interfering radicals, e.g., alkoxyalkyls such as methoxyethyl, hydroxyalkyls such as hydroxypropyl; cyanoalkyls; aralkyls, such as benzyl or α-methylbenzyl; substituted aryls, such as tolyl, xylenyl, isopropylphenyl, t-butylphenyl, or chlorophenyl; and the like. These are given as illustrative only, and are in no way intended to be inclusive of all such compounds.

The dialkyl phosphonate starting material is a compound of the formula:

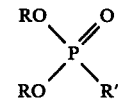

In this structural formula, R' represents alkyl of from 1 to 20 carbon atoms, alkenyl of from 3 to 20 carbon atoms, or aryl of from 6 to 20 carbon atoms which may be mono- or poly-substituted with, e.g., alkyl of from 1 to 4 carbon atoms or halogen. R represents alkyl of from 1 to 4 carbon atoms. Preferably, R' represents alkyl of from 1 to 4 carbon atoms or phenyl. Preferred as R is methyl. Most preferably, the dialkyl phosphonate is dimethyl methylphosphonate. Mixtures of dialkyl phosphonates may also be used.

The copolycondensation reaction can be run without a catalyst, but, to permit lower temperatures and/or shorter reaction times, it is preferably conducted in the presence of a nucleophilic catalyst. Suitable nucleophilic catalysts include alkali metal and alkaline earth compounds conventionally recognized as bases, for example, oxides such as sodium oxide, potassium oxide, magnesium oxide, calcium oxide, and the like; alkali metal and alkaline earth hydroxides, such as sodium hydroxide, potassium hydroxide, magnesium hydroxide, calcium hydroxide, and the like; the corresponding carbonates and bicarbonates, such as sodium carbonate and bicarbonate, potassium carbonate and bicarbonate, magnesium carbonate and bicarbonate, calcium carbonate and bicarbonate, and the like; alkoxides, such as sodium methoxide, potassium ethoxide, magnesium ethoxide, calcium ethoxide, and the like; phenolates, such as sodium phenolate, potassium phenolate, calcium phenolate, and the like; salts of strong bases and weak volatile acids such as alkali metal and alkaline earth metal acetates, phosphates, chlorides, and bromides; and salts of organic phosphorus acids and partial phosphate esters. Organic bases such as amines, for example, pyridine, quinoline, triethylamine, tetramethyl guanidine, N-methylmorpholine, butylamine, aniline, and the like may be used. Additionally, very weak organic bases such as amides, for example N-methylpyrrolidone and hexamethylphosphoric amide, are effective.

The definition of nucleophilic catalyst in the context of the present invention extends to those substances known as "Lewis bases," i.e., electron pair donors, and thus includes, for example, trialkylphosphines, triphenyl phosphines, tributyltin oxide, and the like. Where, for example, the phosphate is a tris(2-haloethyl) phosphate and a catalyst is employed, the true catalyst is believed to be the anion of a salt of bis(2-haloethyl) phosphate prepared in situ by the cleavage of tris(2-haloethyl) phosphate with a salt whose anion is sufficiently nucleophilic to effect the cleavage. Thus, substances not normally considered bases such as alkali metal halides, e.g., sodium chloride, sodium bromide, and the like, potassium chloride, potassium bromide, and the like, are also included within the term "nucleophilic catalyst" as used herein inasmuch as they are sufficiently nucleophilic to effect the desired cleavage. Suitable quantities of catalyst are from a few parts per million, e.g., 50 p.p.m., up to about 10% by weight, preferably 0.01–5% based on the weight of the reaction mixture.

The reaction mixture, with proper amount of catalyst, if desired, and in proper molar ratio of starting materials, is heated to a temperature within the range of from about 110° to about 250° C., preferably 120°–230° C. An alkyl group of the dialkyl phosphonate combines with a halogen atom of the β-haloalkyl phosphate, splitting off an alkyl halide. At the same time, an alkylene linkage is formed between the phosphonate and the phosphate. Thus, in theory, the first reaction scheme is, using a β-haloethyl phosphate as an illustration,

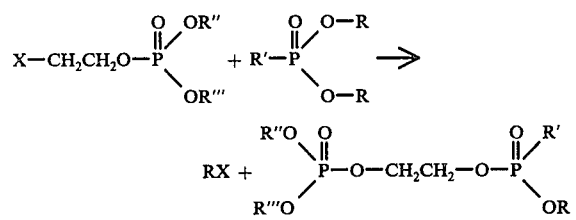

in which X is halogen, R and R' are as defined above, and R" and R''' are the other ester groups on the β-haloalkyl phosphate.

The foregoing scheme represents the reaction which would occur if neither R" nor R''' was a β-haloalkyl group; a product containing two phosphorus atoms is formed, and no further condensation would occur even if there were an excess of unreacted dialkyl phosphonate and reaction conditions were maintained.

If, on the other hand, there are additional β-haloalkyl groups in the phosphate — i.e., if the phosphate were a bis(β-haloalkyl) phosphate or a tris(β-haloalkyl) phosphate — additional condensation could occur if the reaction conditions were maintained. Illustrative of these polycondensation reactions are those shown below. It should be noted that these reaction schemes represent "idealized" situations. Where there is more than one reaction group in the phosphate compound, i.e., in bis(β-haloalkyl) and tris(β-haloalkyl) phosphates, some polycondensation may occur with a portion of the phosphate while another portion thereof may remain unreacted or may form a "lower" condensation product than would be expected from stoichiometrical formulae. Thus, even where only one condensation product formula is hereinafter indicated, it must be realized that this formula represents a major component of the condensation product and that amounts of higher and lower condensation products are generally coproduced, and therefore the products of the process are generally mixtures. Reaction (A): tris(β-chloroethyl) phosphate and dimethyl methyl phosphonate, 2 moles of phosphate per mole of phosphonate

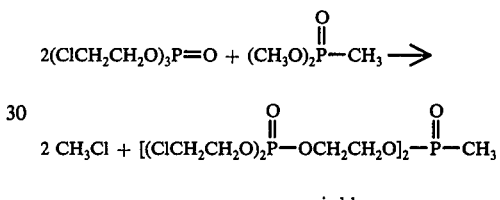

accompanied by some

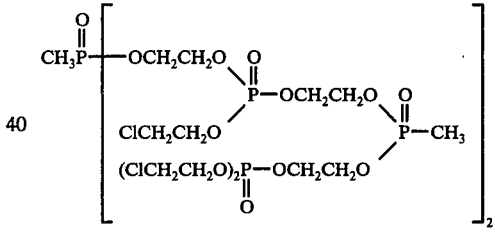

and related higher condensation products, and some ethylene dichloride. Reaction (B): tris (β-chloroethyl) phosphate and dimethyl methyl-phosphonate, in equimolar amounts

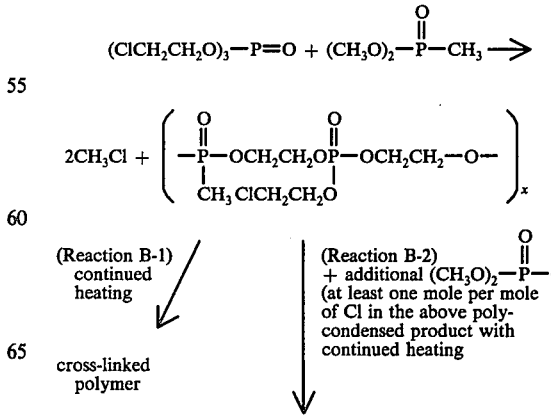

-continued

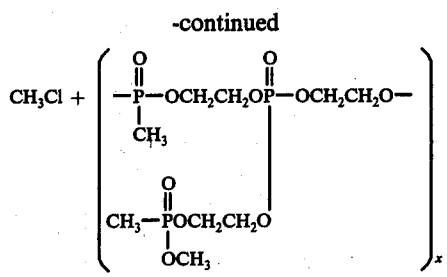

non-crosslinked product.

Reaction (C): tris(β-chloroethyl)phosphate and dimethyl methylphosphonate, 2 moles of phosphonate per mole of phosphate

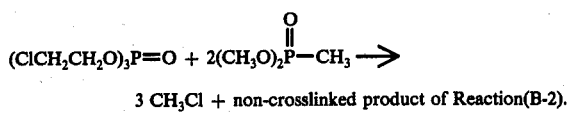

3 CH₃Cl + non-crosslinked product of Reaction(B-2).

Reaction (D): tris(β-chloroethyl) phosphate and dimethyl methyl phosphonate, 3 moles of phosphonate per mole of phosphate

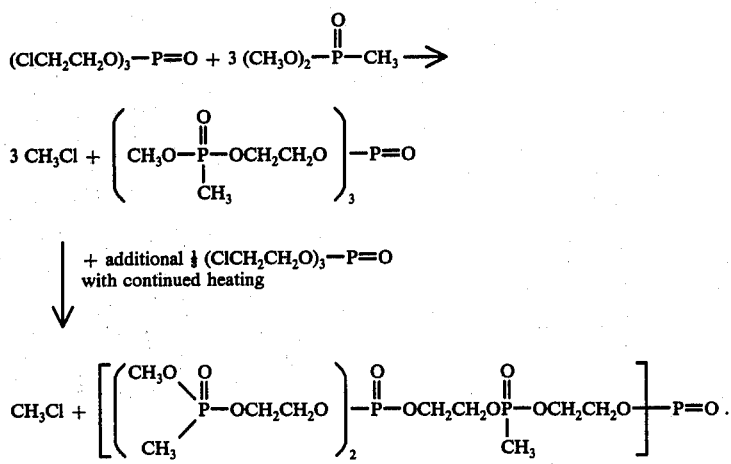

The product is actually a mixture of this condensate and related phosphate-phosphonates of varying degrees of condensation.

Reaction (E): tris (β-chloroethyl phosphate and dimethyl methyl phosphonate, the phosphonate being present in greater than 3 moles per mole of phosphate

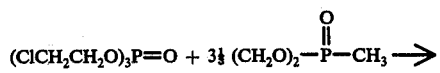

3 CH₃Cl + polycondensate composition of Reaction (D).

Reaction (F): tris(β-chloroisopropyl)phosphate and dimethyl methyl phosphonate, 2 moles of phosphonate per mole of phosphate

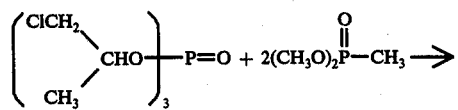

-continued

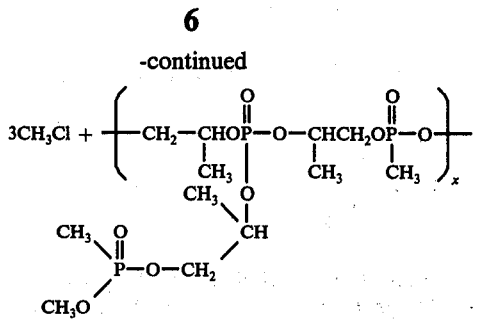

Reaction (G): tris(β-chloroethyl)phosphate and diethyl ethylphosphonate, 2 moles of phosphonate per mole of phosphate

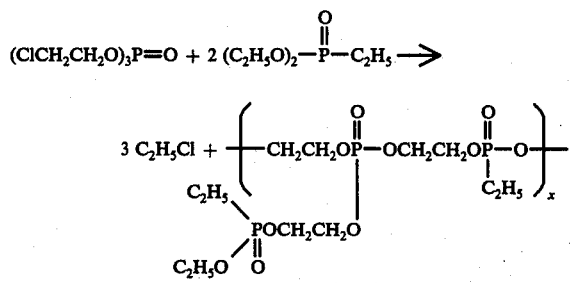

Reaction (H): tris(2,3-dibromo-n-propyl) phosphate and dimethyl methylphosphonate, in equimolar amounts

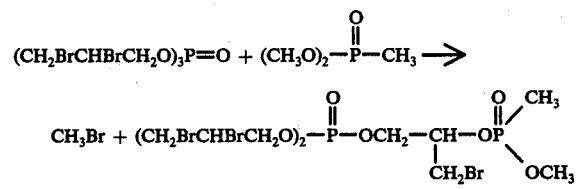

and isomers

Reaction (I): tris(β,β'-dichloroisopropyl) phosphate and dimethyl methylphosphonate, in equimolar amounts

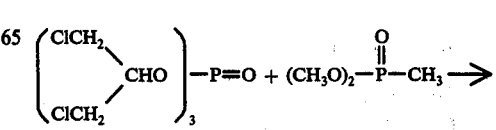

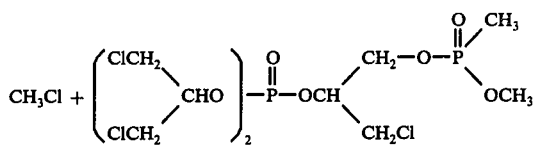

Reaction (J): tris(β-chloroethyl) phosphate and dimethyl phenylphosphonate, 2 moles of phosphonate per moles of phosphate

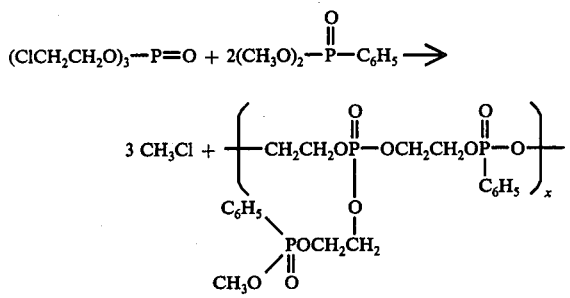

Reaction (K): tris(β-chloroethyl)phosphate and dimethyl methyl phosphonate, 2 moles of phosphonate per mole of phosphate, with additionally 0.01 to 0.1 moles of dimethyl n-octadecyl phosphonate

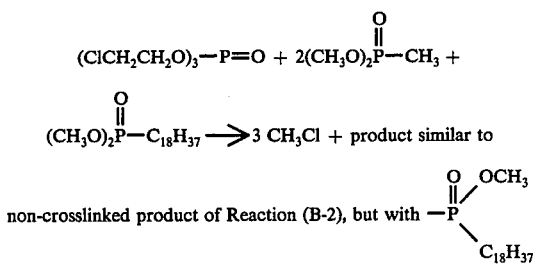

end groups imparting a surfactant character to the polycondensate.

Reaction L: tris(2-chloroethyl) phosphate and dimethyl allylphosphonate, 2 moles of phosphonate per mole of phosphate

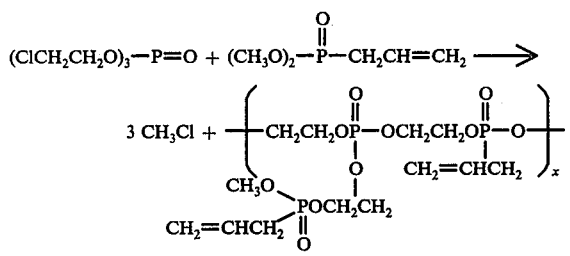

In the foregoing illustrations, the phosphate was usually tris(β-chloroethyl)phosphate and the dialkyl phosphonate was usually dimethyl methylphosphonate. These particular reactants, which are preferred from the economic standpoint, were used here for illustrative purposes only. It will be realized, of course, that analogous products can be obtained by using any of the starting materials included within the ambit of this disclosure.

The condensate products obtained will, as illustrated by the foregoing Reactions (A) through (E), depend largely upon the molar ratio of the phosphonate reactant to the phosphate reactant. Although products of the type illustrated in all five of said reactions are within the scope of this invention, preferred are those made by processes wherein the halogen originally present in the reactant mixture is substantially eliminated as alkyl halide (i.e. down to about 1% halogen or less). In the cases where the reactants are tris(2-haloalkyl) phosphates and dialkyl phosphonates, the preferred cocondensates are those resulting from at least 2 moles of phosphonate per mole of phosphate, in which the polycondensation is carried to the point where essentially all of the halogen (down to about 1% or less) has been driven off as alkyl halide. These preferred products, with the halogen removed, have the multiple advantages of (1) higher percent phosphorus and greater flame retardant efficacy, frequently even more than expected on a phosphorus content basis; (2) resistance to further viscosity increase and gelation on continued heating; (3) less smoke and toxic fumes in processing or combustion of polymers containing these flame retardants. The substantial elimination of halogen as alkyl halide can be accomplished by using ratios of dialkylphosphonate to tris(β-haloalkyl) phosphate of about 2:1 or higher.

In this especially preferred aspect of the invention, the reaction scheme is illustrated by Reactions (B-2), (C), (F), (G), (J), (K) and (L). The symbol x in the product formulae represents the degree of polymerization, which is at least 2 and which would approach infinity as a limit if the reactants were in perfect 2:1 molar ratio and there were no side reactions which produce end groups. In fact, with a molar ratio of 2:1, one obtains products of very high viscosity, up to, for example 40,000 centipoise (25° C.).

In general, the polycondensation reaction scheme for a tris(β-haloalkyl) phosphate and a dialkyl phosphonate, in molar ratio of about 2 moles of phosphonate per mole of phosphate is

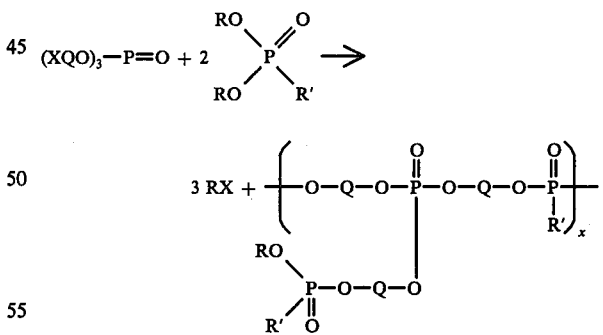

in which R, R' and X are as defined above and Q is alkylene of from 2 to 4 carbon atoms.

Also within the preferred aspect of this invention is the reaction where the molar ratio may be 3 moles of phosphonate per mole of phosphate, and the idealized reaction scheme is

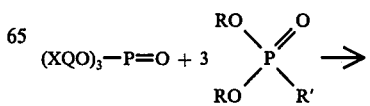

-continued

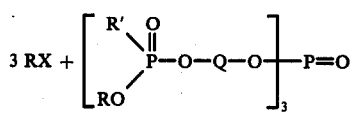

As explained above, however, some higher condensation products will also be formed. This aspect of the invention is illustrated by reactions (D) and (E) above.

Where even higher then a 3:1 ratio of phosphonate to phosphate is used, the formation of higher condensed products (involving displacement of two R groups from some of the phosphonate) will be repressed and the actual results will approach more closely the idealized equation, with excess phosphonate remaining unreacted. The excess phosphonate can be left in or distilled out depending on purity requirements of the product.

A molar ratio of phosphonate to phosphate substantially lower than 2:1, as in reactions (A) and (B-1), represents a nonpreferred aspect of this invention. The products represented by Reaction (A), for example, where the phosphonate to phosphate molar ratio is 1/2:1, are useful flame retardants having much lower volatility than their parent compounds. They are, however, relative to the preferred compounds of this invention, somewhat inferior since, on further heating, they undergo gelation and/or emission of volatile halides.

In the practice of the process for producing the polycondensate products of this invention, the reaction is allowed to proceed until the theoretically produced amount of alkyl halide (e.g., methyl chloride) by-product is obtained. When the polycondensation reaction has been completed, the crude residual product is suitable for use in certain non-critical applications such as thermosetting resin systems (i.e., phenolics or aminoplasts) where volatile and/or acidic components can be tolerated. Since these resins themselves will give off volatile components during curing, and since in such systems acidic components can be tolerated or may even be helpful as cure promotors, the presence of alkyl halide and acidic by-products is often found not to be detrimental.

For applications where volatile components are generally undesired, such as for flame retardant additives used in polyester resins, the residual product can easily be freed of volatiles (e.g., alkyl chloride, alkylene dichloride, and any unreacted starting materials by purging with an inert gas and/or by application of vacuum, with or without heating.

In addition to volatile components, which can easily be removed as indicated, the residual polycondensation products also are generally found to contain by-product acidic structures to some extent. Where the polycondensation products are relatively small molecular weight products such as the sort illustrated by the formulae:

(ClCH₂CH₂O)₂P(O)OCH₂CH₂OP(O)(CH₃)(OCH₃)

or

[(ClCH₂CH₂O)₂P(O)OCH₂CH₂O]₂P(O)CH₃, the product may be freed of acidic by-products by such simple means as washing with an aqueous solution of a base, such as sodium carbonate. However, where the product is a relatively higher molecular weight polymer such as

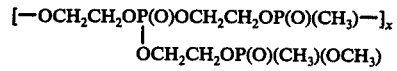

the acidic by-product structures represent end groups on many or most of the polymer chains and removal by simple washing means becomes impracticable.

It is a feature of the present invention that means has been found for substantially neutralizing such acidic byproducts thus rendering them harmless when the polycondensation product is to be used for applications where acid can cause catalysis problems such as in urethane foams or textile finishes. It is a further significant feature of the invention that in the neutralization of said acidic by-products, means has been found for conveniently creating useful functional groups, in particular alcohol end groups. Where said acidic structures occur as end groups on most or all of the polymer chains, the introduction of alcohol end groups makes the polycondensation polymer a "reactive" flame retardant rather than an "additive" flame retardant, i.e., the flame retardant can become attached by the alcohol end group to a polymer matrix such as that of a urethane foam, polyester, aminoplast resin, phenolic resin or the like thus imparting flame retardant properties which are not readily subject to loss resulting from migration, volatility or leaching.

The acidic structures present in the polycondensation products of the invention appear to be of two principal types: (1) true acids and (2) structures which generate acid rapidly in water. Experimental data show that the acid content as determined by titration of the product in water, after a few minutes waiting time, is substantially in excess of the acid content as determined by titration of the product in alcohol solution. It is believed that the difference between these two acid content values is represented by labile cyclic glycol phosphate ester rings illustrated by the structure

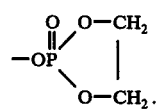

In water these groups open within minutes at room temperature to form true acid groups, exemplified by the formula

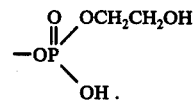

In alcohols, especially in primary alcohols, these cyclic ester groups open to neutral ester groups, exemplified by the formula

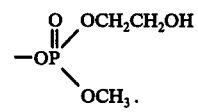

The other acidic structures present in the polycondensation product are believed to be true acidic groups of the type >P(O)OH, and undergo titration with base identically in alcohol or water. Some pyrophosphate structures may also be present in minor amounts.

Several alternatives exist for elimination of these acidic structures from the polycondensation products of the invention. Direct introduction of an alkylene oxide such as ethylene oxide, propylene oxide, butylene oxide, octylene oxide, epichlorohydrin, glycidol, epibromohydrin, styrene oxide, glycidyl ethers such as the diglycidyl ether of bisphenol-A, epoxy cycloalkanes such as epoxycyclohexylmethyl epoxycyclohexylcarboxylate, butadiene diepoxide, vinylcyclohexene diepoxide, 4,4,4-trichloro-1,2-epoxy-butane, or the like will rapidly neutralize the true acid groups, yielding 2-hydroxyalkyl structures in their place, and will slowly neutralize the labile cyclic ester groups by a reaction which stoichiometrically amounts to ring opening of both the cyclic ester and epoxide ring, forming a linear ester structure in their place. Such direct epoxide reactions with the crude (acidi polycondensation products of the invention are useful but tend to be relatively slow and difficult to carry absolutely to completion. An orthoester such as trimethyl orthoformate will neutralize the true acid structures by conversion to ester, but will not eliminate the cyclic esters.

The preferred process for eliminating the acidic structures is a process wherein (1) the labile cyclic ester structures are opened by reaction at ambient temperatures of about 20° to about 180°, preferably 50° to 150°, with a reagent

YOH where Y is alkyl of from 1 to 20 carbon atoms unsubstituted or substituted by noninterfering substituents, and (2) the true acid structures are neutralized by reaction with an epoxide or an orthoester to form ester groups. These two steps can be run concurrently or successively.

As the group Y in the ring-opening reagent, any alkyl or substituted alkyl group may be used so long as the substituent or substituents do not adversely affect the ring-opening reactions and do not cause undesirable side reactions, e.g. reactions with portions of the polycondensation product which would result in a loss of or reduction in fire-retardant propertes. Usable substituents thus include aryloxy, halogen, alkoxy, aryl, acyl, acyloxy, hydroxy, amido, alkylthio, arylthio, carbalkoxy, carboxamido, cyano and nitro. Suitable ring-opening reagents are exemplified by methanol, ethanol, n-butyl alcohol, lauryl alcohol, other monohydric alkanols having from 3 to 12 carbon atoms, allyl alcohol, 2,3-dibromopropanol, tribromoneopentyl alcohol, dibromoneopentylene glycol, ethylene glycol, dibromobutenediol, diethylene glycol, methoxyethanol, ethoxyethanol, butoxyethanol, 2-chloroethanol, benzyl alcohol, glycerol, pentaerythritol, dipentaerythritol, trimethylolethane, trimethylolpropane, sorbitol, glucose, sucrose, lactose, methylglucoside and polyoxyalkylated (especially polyoxyethylated or polyoxy propylated) derivatives of any of the aforementioned polyols, acryloxyethanol, acetoxyethanol, methacryloxyethanol, N-hydroxymethylacrylamide, vinyl hydroxyethyl ether, methylolmelamines, methylolureas, and hydroxymethylphenols.

In addition to the above-described ring-opening reagents water may also be used to open the glycol phosphate ester ring. In this case, the polycondensation product would not be neutralized by the ring-opening reaction and, if neutralization is desired, it will be necessary to react the product with an epoxide or an orthoester group.

This ring opening step allows the introduction of valuable functional groups. Where the polycondensation product is of large molecular size, most of the molecules will be terminated by the aforementioned labile cyclic phosphate ester groups and therefore at least one functional group can be imparted in the ring-opening step to most of the molecules. Through the choice of water, a monohydric alcohol, a diol or a polyol as the ring opening reactant, options are made available as to the average functionality of the product. In the following equations the phosphonate-phosphate chain, such as

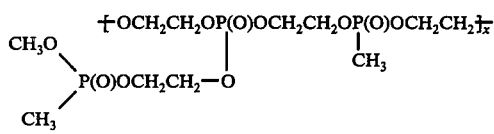

is represented by the symbol Z and the chemistry of the cyclic end group is illustrated by the following reaction schemes:

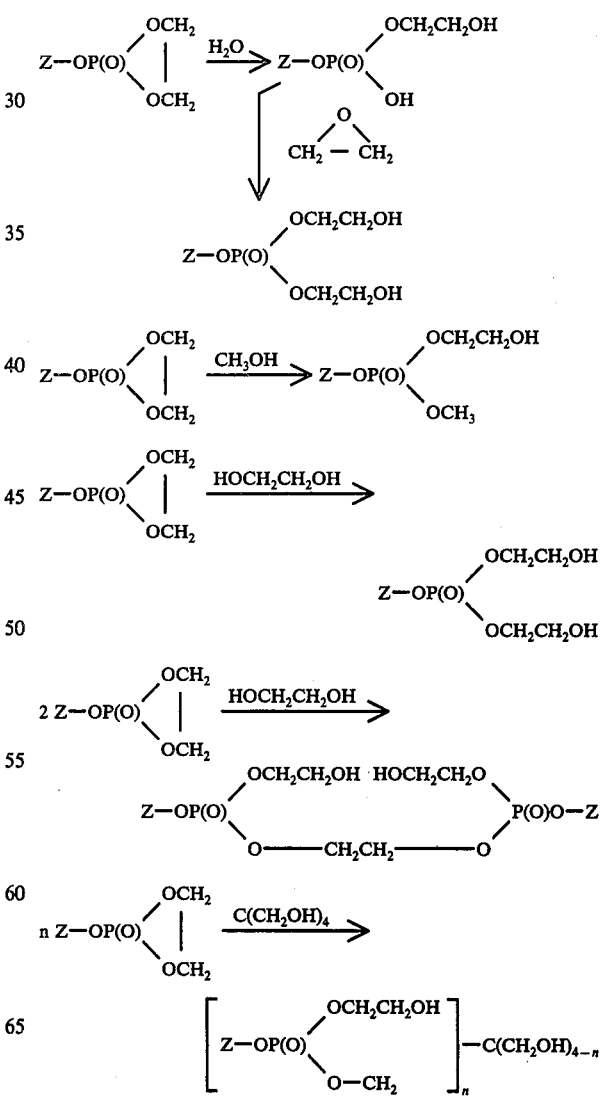

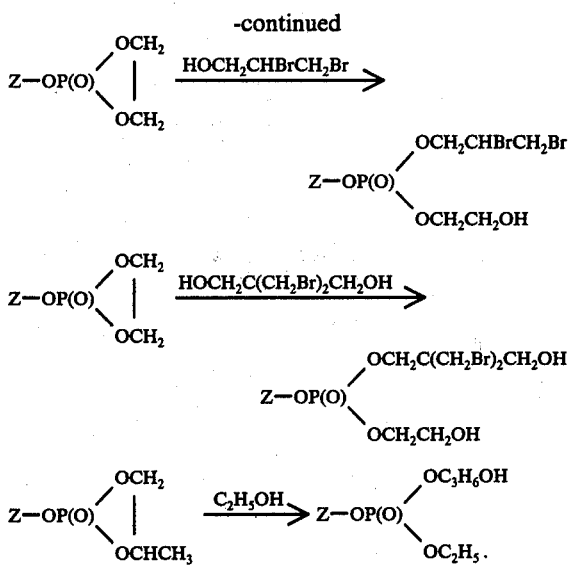

The other end group on Z can be the same as the end group shown, or can be, for example (CH₃O) (CH₃)P(O)— or (HOCH₂CH₂) (CH₃)P(O)—, the latter resulting from (HO) (CH₃)P(O)— plus ethylene oxide. In general, only the average functionality of the products is known, the products being mixtures as heretofore explained.

Neutralization of the true acid structures is accomplished by treatment with an epoxide reagent or an aliphatic orthoester. The epoxide reagent is a compound having one or more

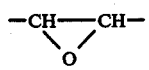

groups. These include the alkylene oxides set forth above. Suitable orthoesters are compounds having a

group in which R is hydrocarbyl, preferably alkyl of from 1 to 6 carbon atoms. Particularly suitable is trimethyl orthoformate. This neutralization reaction may be run at a temperature of from about 25° to about b 225° C, preferably from 50° to 150° C, over a period ranging from 5 minutes to 24 hours.

By means of the Y group introduced in the ring-opening step as well as the 2-hydroxyalkyl groups from the alkylene oxide, the products of the invention can be made to have various controllable degrees of OH functionality, for example, OH numbers (as conventionally defined in terms of mg. KOH/g) in the range of 30–100 for use in flexible urethane foams or above about 100 for use in rigid urethane foams. The OH groups also serve as binding sites for incorporation of these products into durable textile finishes, where a coreactant system such as dimethyloldihydroxyethylene urea plus an acid catalyst, a methylolmelamine, plus an acid catalyst, or N-methylolacrylamide plus a free radical conjointly with an acid catalyst may be employed. Where unsaturated groups are present in the alcohol, as in several listed above, these groups may act as binding sites in polymerizable systems such as polyester resins or textile finishes cured by free-radical means. Where a methylolmelamine, methylolurea or methylolphenol is used as the reactant alcohol, these groups may act as binding sites in related thermosetting resins or resin finishes.

The following examples are here inserted to illustrate the practice of this invention. They are presented here for illustrative purposes only and are not to be construed as limitations.

EXAMPLE 1

This example illustrates the polycondensation reaction in which three methyl methylphosphonate radicals replace three halogen atoms in tris(2-chloroethyl) phosphate. A mixture of 285.5g (1 mole) tris(2-chloroethyl) phosphate, 558g (4.5 moles) dimethyl methylphosphonate and 1g Na₂CO₃ (catalyst) was heated at 158°–196° C. over 4 hours until 3 moles of methyl chloride (identified by boiling point) and a trace of ethylene dichloride were evolved. The reaction mixture was then stripped at a pot temperature of 159° C. at 0.5mm to remove unreacted dimethyl methylphosphonate. The residual clear, colorless liquid, 432g, was neutralized by adding 14g of methanol and heating the mixture for 1 hour at 90°–100° C (to open cyclic glycol phosphate rings) and then passing in ethylene oxide at 90°–110° C. until the acid number was reduced to less than 0.1 mg. KOH/g.

The resultant product was a colorless water-soluble liquid having 24.7% P, 0.1% Cl. Nmr and infrared spectra confirm that the structure is principally:

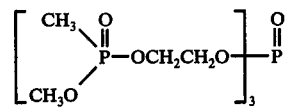

plus small amounts of higher polycondensed oligomers and analogs containing hydroxyethyl groups.

EXAMPLE 2

Evaluation of Product of Example 1 as a Flame Retardant.

At 5 phr in a flexible urethane foam prepared as indicated in Example 5 below, the resultant foam was self-extinguishing and non-burning (SENBR) both before and after the GM cycle, and gave greater than 90% transmittance by the standard fogging test. By contrast, the commercial fire retardant tris(dichloropropyl)phosphate required greater than 10 phr to achieve the same inflammability rating, and failed the fogging test.

In the GM cycle, (General Motors (Fisher Body) aging cycle), flexible foams are subjected to the following sequence of aging: 4 hours at −29° C, 16 hrs. at 38° C (100° F) and 100% relative humidity, 4 hours at −29° C, 16 hr. at 38° C (100° F) and 100% relative humidity, and 72 hour at 93° C (200° F). This entire sequence is then repeated.

The standard fogging test measures fog tendency, which is a tendency of plasticizers, flame retardants, etc., in automobile components — such as vinyl seat coverings and urethane foam cushioning — to cause a fog which in turn causes glare and lack of transparency in the windows. This tendency is measured by placing foam specimens in glass containers in an oven arranged such that the foams are warmed and the glass surfaces are cooled. The amount of loss of transparency is measured. Values above 90% are considered satisfactory; values below 90% are regarded as failures.

EXAMPLE 3

In order to evaluate the advantage of the essentially chlorine-free copolycondensed product of Example 1 in respect to metal corrosion and volatility, the product was heated on a tin-plated steel dish in an oven at 135° C. for three hours. The product lost 8–9% by weight and did not corrode the dish. The homo-polycondensed tris(2-chloroethyl) phosphate, on the other hand, lost 18% by weight and caused considerable corrosion to the dish.

EXAMPLE 4

Preparation and Characterization of 2:1 Dimethyl Methylphosphonate-Tris(2-Chloroethyl)Phosphate Co-Condensation Product A mixture of 2480g (20 moles) of dimethyl methylphosphonate, 2855g (10 moles) of tris(2-chloroethyl) phosphate and 20g of sodium carbonate (catalyst) was stirred and heated in a vessel fitted with a reflux condenser, allowing methyl chloride to escape from the outlet of the reflux condenser. Evolution of methyl chloride (identified by its boiling point) ensued at about 140° C.; the temperature of the reaction mixture was raised over 4½ hours to 183° C. and held about 1 hour until the rate of methyl chloride evolution dwindled to a negligible rate of 0.15g per minute. At this point, the weight loss of the residual reaction mixture was 1503g, corresponding closely to the theoretical 1515g (30 moles) of methyl chloride for the theoretical reaction indicated above.

That the reaction had resulted in the evolution of practically all of the chlorine content of the reactant as volatile methyl chloride was also confirmed by analysis of the residual reaction product for total chlorine, which was found to be only 0.4%.

The product at this point had an acid content of 0.2 meq/g as determined in methanol and a total acid plus cyclic ester content of 0.97 meq/g as determined in water, allowing 10 minutes hydrolysis time before titration; thus the cyclic ester content is estimated by difference to be about 0.77 meq/g. The product at this point is suitable for flame retardant use in systems not sensitive to acid content, for example, in polyester resins, but not generally suitable for use in urethane foams because of the interaction of its acid component with the catalysts used in urethane foam manufacture.

That very little free dimethyl methylphosphonate was present in the product was proved by vacuum stripping to 90° C. at 0.1mm which caused a weight loss of only 4%.

EXAMPLE 5

Conversion of the Product of Example 4 to Neutral Alcohol

The product of Example 4 was admixed with 120g (3.7 moles) of methanol, a small molar excess over the amount of cyclic ester indicated by the titration assay described and heated at 95°–100° C. for 1 hour until the methanolic and aqueous titrations became 0.4 meq/g and 0.24 meq/g respectively, indicating only 0.16 meq/g of cyclic ester remaining. The residual acidity was then eliminated by introduction of ethylene oxide at 90°–97° C. over 5 hours.

The final product was a nearly colorless syrup, viscosity 6000 cps. at 25° C., containing 23.3%P., 0.4% Cl, and having an OH number of 79.8.

When the methanol treatment is omitted and the crude product is treated directly with ethylene oxide to the point of neutrality, the OH number is only 14.5 mg KOH/g. Such a low OH product is suitable as a flame retardant additive for urethane foams but has little bonding capability and can largely be removed by leaching the foam with a solvent.

EXAMPLE 6

Conversion of the Product of Example 4 to a Diol-terminated Analogue of the Product of Example 5

To 600g of the product of Example 4 was admixed 10.6g (0.59 mole) of water, substantially equivalent to the assayed amount of cyclic ester. After heating the mixture at 100° C. for 1 hour, the methanolic and aqueous titrations were found to be 1.04 meq/g and 1.06 meq/g respectively, indicating that essentially all of the cyclic ester had been opened to 2-hydroxyethyl acid phosphate end groups of the structure

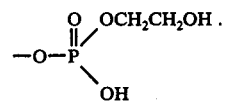

This acid product was neutralized by introduction of ethylene oxide at 100° C. for 5 hours. The resultant product was found to have no acid content or cyclic ester content by methanol, KOH and aqueous NaOH titrations. The OH number of this product was found to be 99 and the %P was found to be 22.0.

EXAMPLE 7

Use of Product of Example 5 in Flexible Urethane Foam as a Permanent Flame Retardant Reaction A urethane foam formulation was made as follows:

|  | Parts by Weight |
|---|---|
| Niax 16–46 polyol, a commercial polypropylene glycol manufactured by Union Carbide Corp. | 100 |
| Water | 4 |
| Flame Retardant Product of Example 5 | 4 |
| Silicone L-548 surfactant, a commercial dimethylsiloxane polymer manufactured by Union Carbide Corp. | 1 |
| Bis(dimethylaminoethyl) ether (catalyst) | 0.1 |
| N-Ethylmorpholine (catalyst) |  |
| Stannous octoate (catalyst) | 0.25 |
| Tolylene Diisocyanate Index | 110 |

A 1/8 lb./cu.ft. foam was obtained containing 0.67% P. This foam was then tested by the method of Federal Motor Vehicle Safety Standard 302 and was found to have a rating of "Self-extinguishing-no burning rate" initially and after dry heat aging at 140° C. for 22 hours and "Self-extinguishing (2.8 inches per minute burn rate)" after 5 hours humid autoclaving at 250° F. Tensile strength was 17.6 lb/sq. in. compared to 18.9 for the comparison foam without flame retardant. In the dry heat aging, a weight loss of only 1.2% was observed, while the foam without flame retardant lost 0.34% and a similar foam flame-retardant with two commercial additive flame retardants (tris)dichloropropyl) phosphate and tetrakis(2-chloroethyl) dichloroneopentylene diphosphate) lost 7.3 and 2.5% respectively. That the product of Example 2 had become bound to the polymer matrix was also shown by methylene chloride extraction of the foam followed by phosphorus analysis, which showed that 91% of the flame retardant was retained, contrasted to 0% and 16% retained in the case of the two additive flame retardants mentioned above. The homo-polycondensed product of tris(2-chloroethyl) phosphate was only retained to the extent of 31% in this test.

In the window-fogging test described in Example 2, the foam made using the product of Example 5 showed 93% retention of window-light transmittance whereas the two additive flame retardants allowed only 40 and 87% transmittance respectively.

EXAMPLE 8

Use of Product of Example 5 in a Polyester Resin

The product of Example 5 was added at 5 phr to a chlorendic-acid-derived polyester resin (Hetron 24370, a product of Hooker Chemical Co.) and the resin cured as a 3-ply glass reinforced laminate (30% glass content) at room temperature using methyl ethyl ketone peroxide and cobalt naphthenate catalyst until a Barcol hardness of 53 was reached. The cured product has an oxygen index of 35.8 and an HLT-15 flame retardant test rating of 100. Substantially lower ratings were obtained using 5 phr of trimethyl phosphate, triethyl phosphate, tris(2-chloroethyl) phosphate, polycondensed tris(2-chloroethyl) phosphate, or the 1:1 copolycondensate of dimethyl methylphosphonate with tris(2-chloroethyl) phosphate (2 moles of $CH_3Cl$ removal per mole of phosphate).

The HLT-15 Flame Retardant Test is a test for flame retardancy of reinforced laminates developed by Hooker Chemical Corp. It is designed to determine the self-extinguishing quality of resins in the form of fiber glass mat reinforced laminates. In the rating systems, the top rating for flame retardancy is given the value of 100. A detailed method of operations and further information concerning this test may be found in a paper by A.J. Hammerl, "Burning Tests for Thermosetting Resins", given at the 17th Annual Technical and Management Conference on Reinforced Plastics, in February, 1962.

Surprisingly, a 72 hour water boil of these polyester laminates removed only 0.54% by weight, which compares favorably with the 3.6—3.8% extraction observed with poly(ethylene methylphosphonate) in an analogous formulation. Since both flame retardants are, themselves, water-soluble, this resistance to leaching from the polyester resin observed with the product of the present invention is surprising and unexpected.

EXAMPLE 9

Preparation of 2.14:1 Mole Ratio Dimethyl Methylphosphonate/ Tris(2-chloroethyl) Phosphate Copolycondensation Product A vessel fitted with stirrer, thermometer, heating mantle, and vertical reflux condenser was charged with 5308g(42.8 moles) of dimethyl methylphosphonate, 5710 g. (20 moles) of tris(2-chloroethyl) phosphate, and 40g. of anhydrous sodium carbonate. After a brief nitrogen purge to remove air (and thus avoid possible oxidative color developmen the reaction mixture was raised to 135°, at which point methyl chloride began to be evolved from the condenser outlet. Over 5 hours the temperature was gradually raised to 185° and held for 27 hours at which time measurement of the rate of methyl chloride evolution showed the rate to have dwindled to 0.18 cc/min. At this point, weighing the remaining reaction mixture showed that a weight loss of 3044g. had occurred, corresponding to 60.3 moles of methyl chloride (as against a theoretical loss of 60 moles). While stirring was continued, the reactor was allowed to cool to about 92° under dry nitrogen. Then 282g. (8.8 moles) of methanol was added over 5 minutes. This quantity was a small excess over the calculated amount of cyclic glycol ester, 7.8 moles, which had been determined to be present by the fact that a sample held for 10 minutes in water and then titrated with 0.1-N NaOH to Bromphenol blue end point showed 1.14 millequivalents of acid plus cyclic ester per gram, whereas a titration of a sample in methanol with methanolic (0.1-N KOH to Bromphenol blue showed 0.16 milliequivalents of acid per gram; thus 0.98 milliequivalents of cyclic glycol ester per gram was present by this assay metnod. The reaction mixture was heated for 2 hours at 95°, at which point the two titration results were 0.27 meq. acid plus cyclic ester per gram and 0.17 meq. acid per gram; thus only 0.10 meq. cyclic ester per gram remained by this assay method. At this point, a fast stream of ethylene oxide was introduced with stirring at 95°. After 4 hours, the titrations by both the aqueous and alcoholic method were nil. Heating was then stopped, ethylene oxide continued as the temperature drifted down to 80°, then vigorous nitrogen sparging was conducted at 90°–95° until dissolved volatiles were removed (found to be mostly dimethyl methylphosphonate). The weight change during this devolatilization step was 3.5%. To remove final traces of acid, which reformed in the devolatilization step, the batch was briefly retreated with ethylene oxide at 95°. Alternatively, 1% of the non-volatile diepoxide of cyclohexenylmethyl cyclohexenylcarboxylate was added. The product, by the ethylene oxide finishing method, had the following characteristics:

Acid No. less than 0.2 mg KOH/g.
OH No. 50±5 mg. KOH/g.
%P= 22.8, 23.0
%Cl= 0.45
Viscosity (25°); 6750 cps. (1/2 hr. sparge at 80° to remove ethylene oxide raised this to 15,500 cps.)
Density: 1.381 (25°)
Refractive Index: 1.4634
Appearance: Clear light yellow syrup Various alternative finishing steps, are described in subsequent examples.

EXAMPLE 10

Cocondensation and Copolycondensation of Dimethyl Methylphosphonate With Tris($\beta'$,$\beta'$-dichloroisopropyl) Phosphate at 1:1 mole Ratio A mixture of 124g. (1 mole) of dimethyl methylphosphonate and 431g. (1 mole) tris($\beta'$,$\beta'$-dichloroisopropyl) phosphate plus 1g. $Na_2CO_3$ catalyst was heated at 190° for 2 hours until 1 mole (50.5g) of methyl chloride was evolved. The residual mixture was then treated with ethylene oxide at 105° C for 4 hours until nearly free of acidity. The elemental analysis of the liquid product corresponded to $CH_3P(O)(OCH_3)$-$OC_3H_5Cl$—$OP(O)(OC_3H_5Cl)_2$. A reaction mixture of the same composition was heated for 8 hours at 184°–186° until 2 moles of methyl chloride were evolved. The elemental analysis of the liquid product corresponded to $[(-P(O)(CH_3)-OC_3H_5Cl-OP(O)-(OC_3H_5Cl_2)(OC_3H_5Cl-)]_x$. Continued heating at 184°–190° led to darkening and finally to gelation. The products of the first two steps were syrups which, when compounded into a cellulose acetate film at 20% (by solvent casting), afforded self-extinguishing characteristics when the film was ignited from the bottom in a vertical configuration.

EXAMPLE 11

Copolycondensation of Dimethyl Methylphosphonate with Tris(2-chloroisopropyl) Phosphate at 2:1 Mole Ratio A mixture of 248g. (2moles) of dimethyl methylphosphonate and 327.5g (1 mole) of tris(2-chloroisopropyl) phosphate plus 1.g of tetraethylammonium chloride as catalyst was heated at 150°–185° until 151 g (approximately 3 moles) of methyl chloride was evolved. The residual liquid is heated with 50 g. of methanol for 2 hrs. at 90° C., then vacuum is applied to remove excess alcohol, then the product is heated with 50 g. of propylene oxide under reflux at 80° until the alcoholic KOH titration declined to less than 1 mg KOH/g. This step requires a substantially shorter reaction time than is required if the alcohol treatment step is omitted. The reaction mixture was then sparged with nitrogen under aspirator vacuum at 80° until it reached constant weight (less than 1 g. weight loss in 1 hr.). The product was a viscous liquid which functioned as a flame retardant when admixed with cellulose acetate (cast film) at 15%.

EXAMPLE 12

Dibromoneopentyl Glycol-Modified Copolycondensation Product

A mixture of 500 g of the crude copolycondensation product of dimethyl methylphosphonate and tris(2-chloroethyl) phosphate (2.14:1 mole ratio, as described in Example 9) and 131 g. dibromoneopentyl glycol was stirred and heated at 98°–100° for 3 hours. At this time, titrations of samples of the reaction mixture to naphtholbenzein end point with alcoholic KOH showed 0.23 meq.acid/g., and titration with aqueous NaOH in water solution showed 0.28 meq. acid/g., indicating that the cyclic phosphate ester content of the crude condensation product had been substantially consumed by reaction with the dibromoneopentyl glycol. The product mixture was then neutralized completely by the passage of ethylene oxide at 90° – 100° for 4 hours. The resultant product was a pale yellowish syrup, completely water soluble, and having 18% P and 12.7% Br content, together with 1.6 millimoles of alcoholic functional groups per gram.

When this product (as an aqueous solution) was padded onto cotton-polyester fabric at 20% dry add-on along with 10% dry add-on N-methylolacrylamide and 1% ammonium persulfate catalyst, and cured at 100°–140° C, the resultant product had excellent flame retardant properties, durable to laundering. Such durable flame retardant finishes are similarly obtained with the products of examples 5, 6 and 9 on cotton, rayon and cotton-polyester fabrics.

EXAMPLE 13

Dibromopropyl - Modified Copolycondensation Product

In like manner to the preceding example, a product is made using 109 g. of 2,3-dibromopropanol in place of the dibromoneopentyl glycol. The resultant product has 18.5% P, 13.1% Br, and 1.6 milliequivalent of OH end groups per gram. It similarly was water-soluble and afforded a durable flame retardant finish when co-cured with N-methylolacrylamide and a persulfate catalyst on cotton polyester fabric. It also affords a durable flame retardant finish on cotton or cotton polyester blends when co-cured with a methylolmelamine or dimethyloldihydroxyethyleneurea and an acid catalyst such as ammonium chloride or zinc nitrate. Typical dry add-ons are 10 – 25% of the phosphorus composition, 5 – 25% of the aminoplast. Typical curing conditions are 100° – 190° C for 0.1 to 15 minutes.

EXAMPLE 14

Tribromoneopentyl-Modified Copolycondensation Product

In like manner to the Example 12, 170 g. of tribromoneopentyl alcohol is reacted with the same crude 2.14:1 copolycondensation product. The end product, although not completely water-soluble, has sufficient emulsifying character to hold the insoluble components in suspension with only gentle agitation. In this form, the product is usable as a flame retardant finish for textiles. It contains 17.9% Br and 16.8%P.

EXAMPLE 15

Use of Ethanol and Various Epoxides in the Neutralization Steps

The crude copolycondensation product of 2.14 moles of dimethyl methylphosphonate and tris(2-chloroethyl)-phosphate of Example 9 was reacted with 10% by weight of ethanol by heating at 95° for 3 hours until the aqueous NaOH and alcoholic KOH titrations becamse almost equal. Two portions of the product were then treated with 3.5% by weight of propylene oxide and 4.5% by weight of epichlorohydrin, each at 95°, until the reaction mixture was substantially neutralized in each case.

EXAMPLE 16

Use of Diethylene Glycol in the Neutralization Step

The crude 2.14:1 dimethyl methylphosphonate/-tris(2-chloroethyl) phosphate copolycondensation product of Example 9 was heated at 95° for one day with 10% by weight of diethylene glycol, until the alcoholic KOH titration and the aqueous NaOH titrations of samples of the mixture became substantially equal. The product was then treated with ethylene oxide at 90°-100°. The resultant clear colorless neutral water-soluble product had an OH number of 82 mg. KOH/g. and was a durable flame retardant when incorporated into a flexible urethane foam at 5 phr.

EXAMPLE 17

Use of Ethanol and a Diepoxide in the Neutralization Steps

A mixture of 500 g. of the crude 2.14:1 copolycondensation product of Example 9, was reacted with 22 g. ethanol at 90–100° for 2 hours. At this point, the alcoholic KOH titration showed 0.245 meq. acid per gram. Therefore, 0.245 millimole of a diepoxide ("ERL-4221", a product of Union Carbide Co., the diepoxide of cyclohexenylmethyl cyclohexene carboxylate) was added per gram of crude product; i.e., 32g. of this diepoxide was added. Heating was continued at 95° C. until the reaction mixture was acid-free. This procedure allows 0.245 millimole of epoxide group per gram to remain unreacted, as a stabilizing acid-acceptor component to prevent development of acidity in storage and handling of the product. The product is usable as a flame retardant reactant in acid-sensitive urethane foam compositions. A similar objective is alternatively accomplished by addition of 0.1–5% of an epoxide, such as the ERC-4221 diepoxide, to the already neutralized copolycondensation products, such as the finished products of Examples 12–16.

Further stabilization in storage and use of this product was accomplished by dissolving in it 0.1% of phenothiazine or an acetone-diphenylamine condensation product, both of which are known antioxidants.

EXAMPLE 18

Preparation of Tris(2-chloroethyl)Phosphate/Dimethyl Methylphosphonate Copolycondensation Product Without Use of Catalyst A mixture of 571 g. of tris(2-chloroethyl) phosphate and 531 g. of dimethyl methylphosphonate was heated at 181°–197° C until 287.5 of methylchloride was evolved; this required 26 hours. The product was then heated at 95° with 28.2 g. of methenol, and finally treated with ethylene oxide at 90 – 100° until substantially neutral. The product was useful as a flame retardant at 5 – 10 phr. in a styrenated polyester.

EXAMPLE 19

Copolycondensation Product Modified by 2-Hydroxyethyl Acrylate and Glycidyl Methacrylate A mixture of 500 g. of the crude 2.14:1 mole ratio copolycondensation product of dimethyl methylphosphonate and tris(2-chloroethyl) phosphate of Example 9 plus 55 g. of 2-hydroxyethyl acrylate and 0.05 g. of methoxyphenol (as polymerization inhibitor) was heated at 90° – 100° for 4½ hours. 28.4 g. of glycidyl methacrylate was then added and the mixture was heated for 2 hours at 90° – 100°. The resultant clear product could be copolymerized in bulk with 10 parts per hundred of methyl methacrylate by heating at 80°–105° with a catalytic amount of azobisisobutyronitrile (200 ppm) to afford a self-extinguishing casting. A similar product, affording a lower degree of cross-linking, was obtained by using ethylene oxide in place of glycidyl methacrylate.

EXAMPLE 20

Copolycondensation Product Modified by 2-Hydroxyethyl Carbamate and the Methylolation Product Thereof A mixture of 500 g. of the same crude copolycondensation product as in the preceding example plus 52.5 g. of 2-hydroxyethyl carbamate was heated at 90° – 95° for 12 hours, then ethylene oxide was passed in for 3 hours at 90° – 95°. The resultant product showed typical -NH$_2$ spectral bands at 1612-1618, 3200 and 3380 cm$^{-1}$. To this product was added 30 g. of paraformaldehyde and 10 cc. of triethylamine (as catalyst), and the mixture heated at 95° – 100° for 3 hours at which point all of the paraformaldehyde had dissolved. The infrared spectrum at this point showed no NH$_2$ bands at 3200, 3380 or 1612 – 1618 cm$^{-1}$ but instead, had NH bands at 1522-1530 and a large OH at 3280-3360 cm$^{-1}$. This product, applied in water solution, along with 1% ammonium chloride, to cotton cloth at 20% dry add-on and cured at 130°–150° C for 5 min., affords a durable flame retardant finish.

EXAMPLE 21

Copolycondensation Product Modified by N-Methylolacrylamide

A mixture of 500 g. of the crude copolycondensation product of Example 9, plus 50.5 g. of anhydrous N-methylolacrylamide and 0.5 g. of p-methoxyphenol (as inhibitor) was stirred and heated at 88°–91° for 2 hours while bubbling air through the mixture to further inhibit polymerization. The product was centrifuged to remove some solid polymeric by-product. The supernatant syrup was water-soluble.

When applied (in aqueous solution) to cotton cloth at 20% dry add-on along with 1% potassium persulfate and polymerized thereon by exposure to superheated steam, a durable flame-retardant finish is obtained.

EXAMPLE 22

Copolycondensation Product Modified by Pentaerythritol

A mixture of 760 g. of the crude copolycondensation product of Example 9 plus 49 g. of pentaerythritol (1 mole for 2 molar equivalents of cyclic ester as determined by alcohol KOH and aqueous NaOH titrations) was heated at 95°–105° for 3 hours. At this point, the alcoholic KOH titration and aqueous NaOH titration were found to be approximately equivalent (0.2 meq/g.). The reaction mixture was then treated with ethylene oxide for 4½ hours at 90°–100° until it was acid-free. The product was a water soluble syrup of 26,000 cps. viscosity at 25°.

It is an effective flame retardant at 5-15 phr in a rigid urethane foam.

EXAMPLE 23

Copolycondensation Product of the Invention in a Melamineformaldehyde Resin-impregnated Paper An admixture of 0.75 parts of the 2.14:1 dimethylmethylphosphonate/tris(2-chloroethyl) phosphate copolycondensation product of Example 9 with 2 parts of melamineformaldehyde resin was dissolved at 12% total concentration in ethanol applied to paper of the type used in automotive air filters. The impregnated paper was then dried and cured at 177° C for 10 minutes. Essentially no smoke or visible vapors were emitted during the curing process. The resultant paper containing the cured resin and flame retardant was found to be self-extinguishing when ignited from the bottom in a vertical position. To achieve the same level of flame retardancy a higher level was required of the homopolycondensation product of tris(2-chloroethyl) phosphate, and a significant amount of visible vapor and ethylene dichloride was evolved from the latter. Likewise, a higher level was required and considerable visible vapor was evolved under these cure conditions using a commercially available oligomeric 2-chloroethyl phosphonate (Phosgard C22R, a product of the Monsanto Company) as flame-retardant.

When the alcohol treatment step used in the preparation of the copolycondensation product is omitted, excessively fast and variable cure times are the result when the product is used as described above.

EXAMPLE 24

Allylation of a Copolycondensation Product of a Phosphonate and Phosphate, and Subsequent Bromination To 100 parts by weight of crude 2.14:1 copolycondensation product of dimethyl methylphosphonate and tris(2-chloroethyl) phosphate (prepared as in Example 9) at 150°–167° was slowly added (over 8 hours) 10 parts by weight of allyl chloride, this amount being calculated as equimolar to the $CH_3$-O-P groups in the copolycondensate. The evolved methyl chloride was separated continuously by means of a fractionating column which caused 30% of the added allyl chloride to be retained and to be reacted. The resultant viscous liquid product in the reactor was found by infrared and n.m.r. spectroscopy to have practically all of the original $CH_3$-O-P groups replaced by $CH_2$=$CHCH_2$O-P groups.

This product when dissolved in water and applied at 20% dry add-on onto cotton cloth along with N-methylolacrylamide at 10% dry add-on plus 0.5% potassium persulfate catalyst, and then dried and cured at 100°–150° C, afforded a durable flame retardant finish.

This product can also be additively brominated to afford a water-soluble bromine-phosphorus finishing reagent for the flame-retarding of cotton-polyester fabric. The allylated product was treated with 17 wt.% of elemental bromine, and allowed to stand at ambient temperature until reaction was completed. After sparging and subjecting the product to the methanol and ethylene oxide steps as described in preceding examples, a neutral water-soluble gray syrup was obtained. Addition of 1% by weight of 70% hydrogen peroxide reduced the color.

As illustrated by the examples above, the products of the invention have broad utility and high efficiency as flame retardants for plastic elastomers, coatings, adhesives, and textiles. In general any physically appropriate mode of incorporation of these products as additives may be employed. In the case of plastics they may be admixed in the melt, added to a solution, or blended with the solid plastic before casting, extrusion, molding, calendaring, coating, impregnating, vulcanizing, or other processing. Generally, effective amounts will be found within the range of 2% to 50%, depending on the nature of the substrate and the degree of flame retardancy required as will be readily understood by those skilled in the art of flame retardancy.

Many variations of the process and products of the invention are possible. For example, one can include, in addition to the phosphate and phosphonate reactants, an aliphatic dihalide having both halogen atoms located on primary carbon atoms. Suitable aliphatic dihalides include compounds of the structure X-alkylene-X, X-$CH_2CH$=$CHCH_2$X, and X-$CH_2CH_2(OCH_2CH_2)_n$X ($n$ = 0 to 4) and X-$CH_2CH_2$-O-$CH_2$-O$CH_2CH_2$X where the alkylene group is of 2 to 10 carbon atoms; suitable species are $BrCH_2CH_2Br$, $ClCH_2Cl$, $ClCH_2CH$=$CHCH_2Cl$, and $ClCH_2CH_2OCH_2OCH_2CH_2Cl$. The aliphatic dihalide may be substituted for part of the $(XCH_2CH_2O)_3P$=O reactant. Where X-$CH_2CH$=$CHCH_2$X is used, the final product may be additively brominated to enhance the flame retardant effect. A further variant on the process and products of the invention is the inclusion, amongst the reactants, of a primary aliphatic halide, alkenyl halide, (i.e., vinyl methyl halide), or benzyl halide. By use of a saturated primary alkyl halide, such as n- or isobutyl chloride chain ends are produced and by this means, the molecular weight of the product may be deliberately limited for example, in order to obtain a less viscous product. By use of a higher alkyl halide, such as lauryl chloride, the products acquire a surfactant character due to their possession of a lipid group on a hydrophilic polymer chain. By us of an unsaturated alkenyl halide such as allyl chloride, or vinylbenzyl chloride, polymerizability and copolymerizability may be imparted to the product permitting its use as a cross-linkable monomer in, for example, polyester resins, or sites for additions of bromine may be supplied. By use of a benzyl halide such as benzyl chloride better solubility in, for example, styrene or methyl methacrylate, or polymers thereof, may be imparted.

What is claimed is:

1. A copolycondensation product of a β-haloalkyl phosphate having from 2 to 4 carbon atoms in the alkyl moiety and a dialkyl phosphonate of the formula

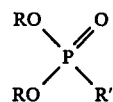

in which R' is alkyl of from 1 to 20 carbon atoms, alkenyl of from 3 to 20 carbon atoms, or phenyl optionally substituted with alkyl of from 1 to 4 carbon atoms and/or halogen, and R is alkyl of from 1 to 4 carbon atoms, said product being obtained by heating the phosphate with the dialkyl phosphonate until at least about one molar equivalent of alkyl halide is evolved.

2. A copolycondensation product according to claim 1 in which the β-haloalkyl phosphate is a tris(β-haloalkyl) phosphate in which the halogen is chlorine or bromine.

3. A copolycondensation product according to claim 2 in which the tris(β-haloalkyl)phosphate is tris(2-chloroethyl)phosphate.

4. A copolycondensation product according to claim 1 in which, in the dialkyl phosphonate, R' is alkyl of from 1 to 4 carbon atoms or phenyl.

5. A copolycondensation product according to claim 4 in which the dialkyl phosphonate is dimethyl methylphosphonate.

6. The copolycondensation product according to claim 1 in which the dialkyl phosphonate is dimethyl methylphosphonate and the β-haloalkyl phosphate is tris(2-chloroethyl) phosphate.

7. A copolycondensation product according to claim 1 in which the heating takes place in the presence of a nucleophilic catalyst.

8. A copolycondensation product according to claim 7 in which heating is effected to a temperature of from about 110° to about 250° C.

9. A copolycondensation product of a tris(β-haloalkyl) phosphate having from 2 to 4 carbon atoms in each alkyl moiety and a dialkyl phosphonate of the formula

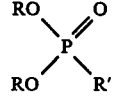

in which R' is alkyl of from 1 to 20 carbon atoms, alkenyl of from 3 to 20 carbon atoms, or phenyl optionally substituted with alkyl of from 1 to 4 carbon atoms and- /or halogen, and R is alkyl of from 1 to 4 carbon atoms, said product being obtained by heating the phosphate with at least 2 moles and less than about 3 moles of the dialkyl phosphonate per mole of phosphate.

10. A copolycondensation product according to claim 9 in which the heating takes place in the presence of nucleophilic catalyst.

11. A copolycondensation product according to claim 10 in which, in the dialkyl phosphonate, R' is alkyl of from 1 to 4 carbon atoms or phenyl.

12. A copolycondensation product according to claim 10, in which the dialkyl phosphonate is dimethyl methylphosphonate.

13. A copolycondensation product according to claim 10, in which the tris(β-haloalkyl) phosphate is tris(2-chloroethyl) phosphate.

14. A copolycondensation product according to claim 10 in which the tris(β-haloalkyl) phosphate is tris(2-chloroethyl) phosphate and the dialkyl phosphonate is dimethyl methylphosphonate.

15. A copolycondensation product according to claim 14 in which the heating is done at a temperature of from about 110° to about 250° C.

16. A copolycondensation product of a tris(β-haloalkyl) phosphate and a dialkyl phosphonate consisting essentially of a polymer having repeating units of the structure

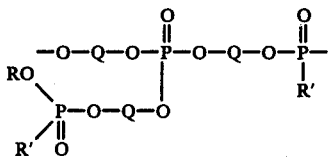

in which Q is alkylene of from 2 to 4 carbon atoms, R is alkyl of from 1 to 4 carbon atoms and R' is alkyl of from 1 to 20 carbon atoms, alkenyl of from 3 to 20 carbon atoms, or phenyl optionally substituted with alkyl of from 1 to 4 carbon atoms, said copolycondensation product obtained by heating a tris(β-haloalkyl) phosphate of the formula

(XQO)$_3$P=O in which X is halogen with a dialkyl phosphonate of the formula

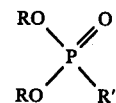

in the ratio of about 2 moles of dialkyl phosphonate per mole of tris(β-haloalkyl) phosphate.

17. A copolycondensation product according to claim 16 in which the heating takes place in the presence of a nucleophilic catalyst.

18. A copolycondensation product according to claim 17 in which R' is alkyl of from 1 to 4 carbon atoms or phenyl.

19. A copolycondensation product according to claim 18 in which R and R' are methyl.

20. A copolycondensation product according to claim 18 in which Q is ethylene and X is chlorine.

21. A copolycondensation product according to claim 17 in which Q is ethylene, X is chlorine, and R and R' are methyl.

22. A copolycondensation product according to claim 21 in which heating is effected to a temperature of from about 110° to about 250° C.

23. A polymer having repeating units of the structure

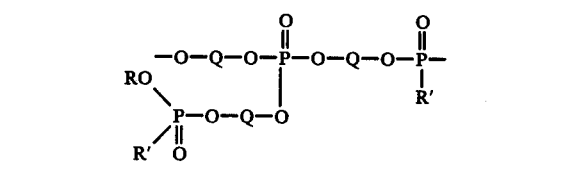

in which Q is alkylene of from 2 to 4 carbon atoms, R is alkyl of from 1 to 4 carbon atoms and R' is alkyl of from 1 to 20 carbon atoms, alkenyl of from 3 to 20 carbon atoms or phenyl optionally substituted with alkyl of from 1 to 4 carbon atoms.

24. A polymer according to claim 23 in which R' is alkyl of from 1 to 4 carbon atoms or phenyl.

25. A polymer according to claim 24 in which Q is ethylene and R and R' are methyl.

* * * * *

UNITED STATES PATENT AND TRADEMARK OFFICE
CERTIFICATE OF CORRECTION

PATENT NO. : 4,086,303
DATED : 4/25/78
INVENTOR(S) : Edward D. Weil

It is certified that error appears in the above-identified patent and that said Letters Patent are hereby corrected as shown below:

Col. 2, line 22, delete "now abandoned,";

Col. 9, line 11, "then" should be ---than--;

Col. 11, line 19, "(acidi" should be --(acidic)--;

Col. 13, line 47, "about b    should be --about--;

Col. 16, line 59, "17.6" should be ---17.7---;

Col. 17, line 62, "developmen" should be --development--;

Col. 18, line 14, "(0.1-N" should be --0.1-N--;

Col. 18, line 17, "methnod" should be --method--;

Col. 20, line 33, "becamse" should be --became--;

Col. 21, line 41, "coploymerized" should be --copolymerized--;

Col. 24, line 7, "us" should be --use--;

Signed and Sealed this

Sixth Day of March 1979

[SEAL]

Attest:

RUTH C. MASON
Attesting Officer

DONALD W. BANNER
Commissioner of Patents and Trademarks